United States Patent [19]

Zuk, Jr.

[11] Patent Number: 5,779,902
[45] Date of Patent: Jul. 14, 1998

[54] IN-LINE VENT FILTER FOR AUTOMATICALLY DRAINING A BIOLOGICAL LIQUID FILTRATION DEVICE

[75] Inventor: Peter Zuk, Jr., Harvard, Mass.

[73] Assignee: HemaSure, Inc., Marlborough, Mass.

[21] Appl. No.: 903,271

[22] Filed: Jul. 25, 1997

Related U.S. Application Data

[63] Continuation of Ser. No. 661,804, Jun. 11, 1996, abandoned, which is a continuation of Ser. No. 449,362, May 24, 1995, abandoned, which is a division of Ser. No. 209,523, Mar. 10, 1994, Pat. No. 5,472,605.

[51] Int. Cl.$^6$ .................... B01D 35/01; B01D 46/00
[52] U.S. Cl. .................... 210/436; 210/252; 210/455; 210/472
[58] Field of Search .................... 210/435, 436, 210/446, 448, 455, 472, 252; 55/385.4, 421; 604/324, 405, 406, 251, 255, 257

[56] References Cited

U.S. PATENT DOCUMENTS

| | | | |
|---|---|---|---|
| 1,844,342 | 2/1932 | Berman | 604/251 |
| 3,523,408 | 8/1970 | Rosenberg . | |
| 3,631,654 | 1/1972 | Riely . | |
| 3,803,810 | 4/1974 | Rosenberg . | |
| 3,881,640 | 5/1975 | Noble | 210/446 |
| 3,967,620 | 7/1976 | Noiles | 210/446 |
| 4,126,558 | 11/1978 | Luceyk | 210/429 |
| 4,276,170 | 6/1981 | Vaillancourt | 210/463 |
| 4,294,594 | 10/1981 | Sloane, Jr. et al. | 210/446 |
| 4,298,358 | 11/1981 | Ruschke | 210/436 |
| 4,341,538 | 7/1982 | Vadnay et al. | 210/436 |
| 4,515,606 | 5/1985 | deWinter | 55/159 |
| 4,525,182 | 6/1985 | Rising et al. | 210/436 |
| 4,568,366 | 2/1986 | Frederick et al. | 210/436 |
| 5,252,222 | 10/1993 | Matkovich et al. | 210/436 |
| 5,437,655 | 8/1995 | Bartholomew | 210/472 |
| 5,439,587 | 8/1995 | Stankowski et al. | 210/472 |
| 5,451,321 | 9/1995 | Matkovich | 210/641 |
| 5,468,388 | 11/1995 | Goddard et al. | 210/446 |
| 5,536,413 | 7/1996 | Bormann et al. | 210/436 |

Primary Examiner—John Kim
Attorney, Agent, or Firm—Heslin & Rothenberg, P.C.

[57] ABSTRACT

A liquid filtration device useable for removing leukocytes from blood is disclosed. Located in-line on the upstream side of the filtration device is a vent device which is configured to allow liquid being filtered to flow therethrough and creates a pressure head sufficient to prevent air from entering the vent until the fluid flow therethrough stops and thereby allows air to automatically enter the vent to allow the air to drain liquid through the filtration device. The vent minimizes air entering the filtration system during the flow of liquid flow therethrough while automatically allowing air to enter the system and thereby drain the system when the flow of fluid stops.

11 Claims, 15 Drawing Sheets

5,779,902

IN-LINE VENT FILTER FOR AUTOMATICALLY DRAINING A BIOLOGICAL LIQUID FILTRATION DEVICE

This application is a continuation of application Ser. No. 08/661,804 filed Jun. 11, 1996, now abandoned, which is a continuation of U.S. application Ser. No. 08/449,362, filed on May 24, 1995, abandoned, which is a divisional of U.S. application Ser. No. 08/209,523, filed Mar. 10, 1994, now U.S. Pat. No. 5,472,605.

FIELD OF THE INVENTION

This invention relates generally to gravity feed liquid filtration devices. More particularly, this invention relates to a gravity feed liquid filtration device useable to filter blood and blood components.

BACKGROUND OF THE INVENTION

At the present time there are several disposable gravity feed blood filtration devices. All of these devices, however, require user manipulation of vent filters during the filtration process. The manipulation of the vent filters must take place at the proper time during the filtration process or the system will not filter properly and the blood being filtered may be rendered unusable. Since, user manipulation of vent filters is time consuming and costly, it is desirable to achieve a liquid filtration device which may filter blood without the manipulation of vent filters.

SUMMARY OF THE INVENTION

The shortcomings of the prior art may be alleviated using a filtration device constructed in accordance with the principles of the present invention. The filtration device is capable of filtering blood to remove leukocytes and other blood components therefrom. The filtration device includes a first chamber capable of collecting unfiltered liquid therein and a second chamber in fluid flow relationship with the first chamber; a means for filtering fluid within the first chamber prior to flowing into the second chamber; a passage leading from the second chamber into the first chamber; means for preventing unfiltered liquid within the first chamber from flowing through the passage into the second chamber, and a first outlet in the second chamber.

The filtration device may further include a second outlet in the second chamber which is located above the first outlet, and a hydrophilic filter oriented to prevent air to flow through the second outlet after the hydrophobic filter becomes wet.

The means for preventing unfiltered liquid within the first chamber from flowing through the passage into the second chamber may include a hydrophobic filter. The means for filtering fluid within the first chamber may include at least one filtration element. When used for filtering blood, the at least one filtration element may include a plurality of leukocyte removing elements.

The first chamber and second chamber may be located within a housing formed by a first section and a second section. The at least one filtration element may be located between the first section and second section extending within an interior of the housing forming a barrier dividing the interior of the housing into the first chamber and second chamber. The at least one filtration element may form an interior wall within the housing. The edges of the at least one filtration element may be located between the first section and second section forming a pinch type seal in between.

The passage leading from the second chamber into the first chamber may extend through the at least one filtration element and may be formed by a tube affixed to the second section.

The filtration device may further include a means for preventing unfiltered fluid from entering the second chamber by flowing between the tube and the at least one filtration element. The preventing means may include a washer mounted on the tube wherein the at least one filtration element is located between the lip on the tube and the washer. The tube may include a lip which contacts the at least one filtration element. The hydrophobic filter may be sealed to an opening of the tube. The hydrophilic filter may be sealed to the second section at the second outlet thereof.

The filtration device may further include a means for placing the first outlet in fluid flow relationship with the second outlet. The means may comprise a conduit which may be integrally formed to a housing defining at least one of the chambers. Tubing may be connected to the conduit for allowing filtered fluid to flow into a fluid collecting means. The filtration device may also include a means for venting unfiltered fluid. This venting means may include an in line vent filter which may be placed in fluid flow relationship with the first chamber between a blood, or other liquid, supply and the first chamber.

One or more flanged washers may be used as the means for preventing unfiltered fluid from entering the second chamber by flowing between the tube and the at least one filtration element. Also, the edges of the at least one filtration element may be sealed to the second section using at least one flanged ring. Any edges, including edges located around the tube, of the at least one filtration element may be heat sealed using a thermoplastic film between layers of edges of more than one filtration element.

The in-line vent filter in accordance with the principles of the present invention includes a body having an inlet and outlet therein, at least one vent opening within the body, and at least one hydrophobic filter oriented to prevent fluid within the body from passing through the at least one vent opening. The hydrophobic filter may be sealed to the body and may include an opening coaxially oriented with the inlet. The body may include an inlet half and outlet half which are sealed together. The body may also include one or more ribs for supporting the hydrophobic filter. The body may also include a restriction.

BRIEF DESCRIPTION OF THE DRAWINGS

The invention may best be understood by reference to the detailed description of the preferred embodiments herein when read in conjunction with the drawings in which.

DESCRIPTION OF THE PREFERRED EMBODIMENTS

Figure 2:
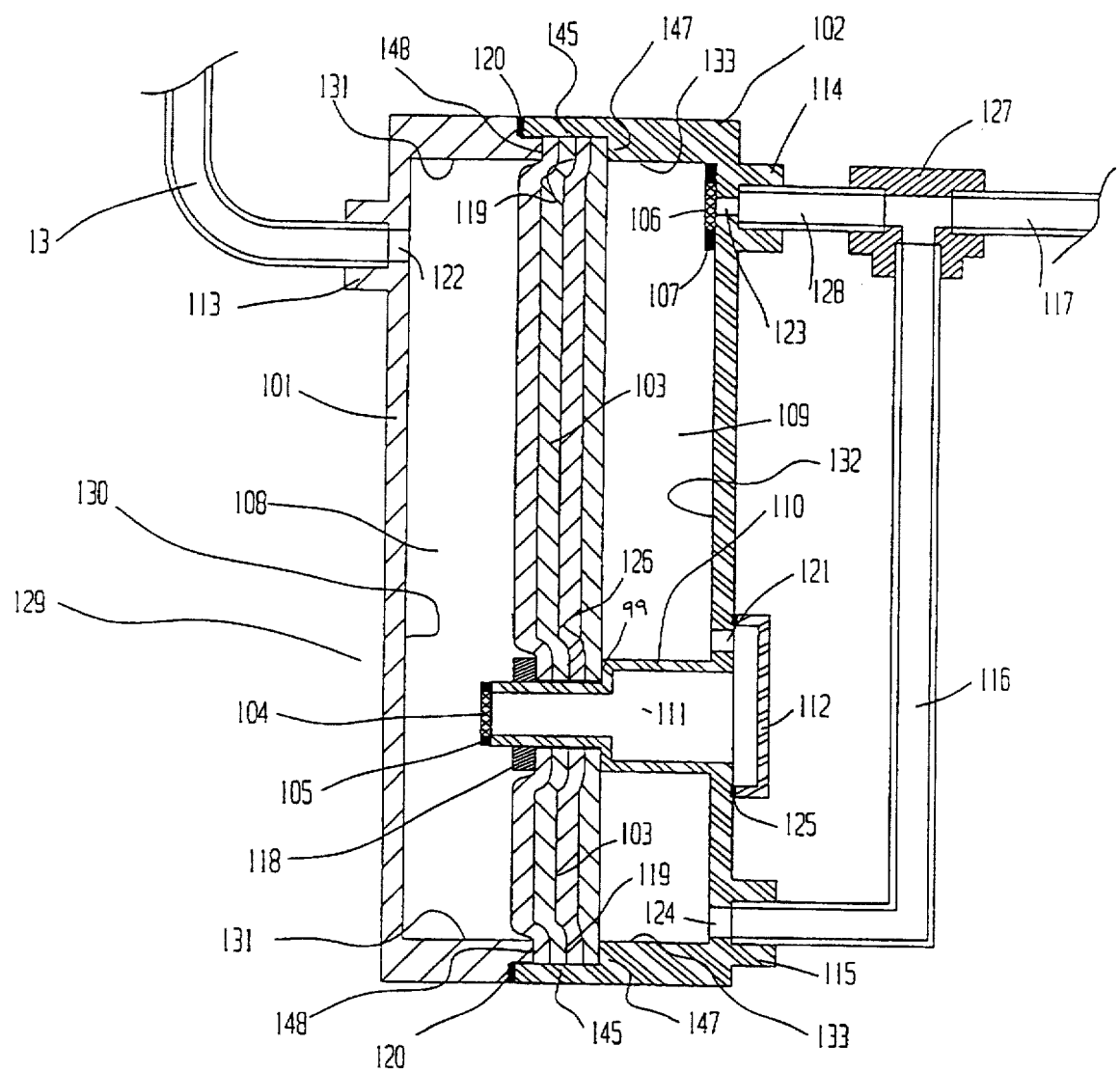
FIG. 2 depicts a schematic sectional representation of a filtration device constructed in accordance with the principles of the present invention.

The liquid filtration device constructed in accordance with the principles of the present invention utilizes an air venting means operatively engaged to a fluid filtration means. One embodiment of the filtration apparatus constructed in accordance with the principles of the present invention is shown in FIG. 2, and its operation depicted in FIGS. 3 and 4.

Figure 1A:
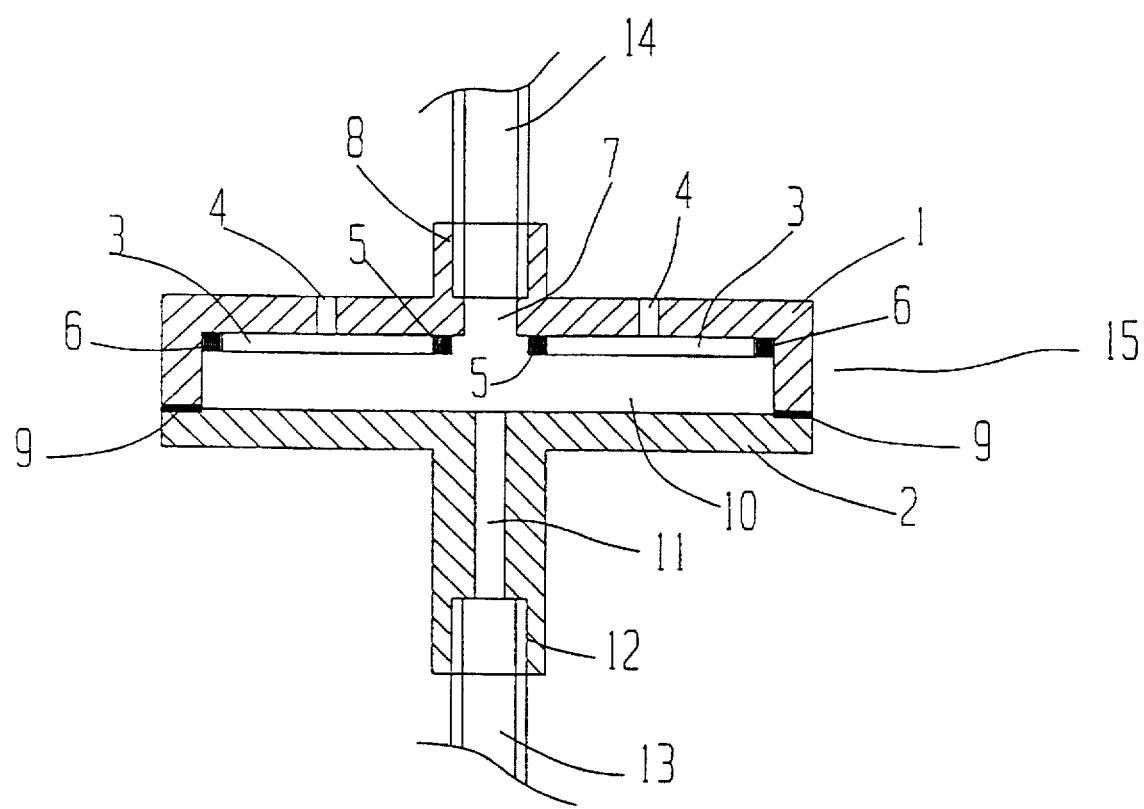
FIG. 1A depicts a sectional representation of an in line vent filter useable in accordance with the principles of the present invention.

FIG. 1A depicts a schematic representation of an in line vent filter 15 useable as an air venting means in accordance with the principles of the present invention. As described herein the automatic in-line vent filter automatically vents the inlet of the fluid filtration system when fluid stops flowing from feed blood bag 20. When fluid flows from feed blood bag 20 the in-line vent filter 15 automatically stops venting. This vent filter may consist of an inlet section 1, an outlet section 2, and a sterilizing grade hydrophobic filter 3. The hydrophobic filter prevents the passage of liquid therethrough, (assuming the liquid is at a pressure less than the bubble point pressure of the filter material) while allowing the passage of air therethrough. Air is capable of passing through the hydrophobic filter even after the filter has been exposed to a liquid. The inlet section 1 may include vent ports 4 which are in air flow relationship to the outside of the vent filter. The hydrophobic filter 3 is sealed to the inlet section 1 by seals 5 and 6, which are preferably heat seals. However, any type of reliable leak proof seals which are well known in the art, such as ultrasonic, solvent or adhesive type seals may be used in accordance with the invention. The in-line vent filter 15 may be a round device and the hydrophobic filter may be shaped as a disc with a hole punched in its center. However, the in-line vent filter 15 is not limited to any particular shape and may include more than one hydrophobic filter 3. Seal 5 should extend around the entire periphery of the center hole of the hydrophobic filter 3 and hence around the entire periphery of a port 7 sealing the hydrophobic filter 3 to the inlet section 1. Seal 6 seals the hydrophobic filter to the inlet section 1 around the entire outer periphery of the hydrophobic filter 3. Although liquid within the chamber 10 may not pass through the hydrophobic filter 3, air may enter vent ports 4 and pass through hydrophobic filter 3. The inlet section 1 of the vent filter may also include a tubing socket 8 into which a length of tubing 14 may be inserted. The tubing socket 8 is in fluid flow relationship with the port 7 which should be approximately the same diameter as the inside diameter of tubing 14.

The outlet section 2 may be bonded to the inlet section 1 by a seal 9. Seal 9 should extend around the entire periphery of the vent filter 15 thus forming chamber 10. Seal 9 is preferably an ultrasonic seal. However, other seals including heat seals, adhesive seals or any other hermetic seal may be used. Outlet section 2 includes restriction 11 forming an outlet of chamber 10, and tubing socket 12 extending from the restriction 11 into which a length of tubing 13 may be inserted. Restriction 11 is typically a long small diameter port which connects chamber 10 to tubing 13. The cross sectioned area of the restriction should be less than the cross sectioned area of the inlet to allow fluid flowing therethrough to fill chamber 10 and contact hydrophobic filter 3.

Liquid to be filtered enters the vent filter 15 via tubing 14 and port 7 and exits via restriction 11 and tubing 13. The length and diameter of restriction 11 depends upon viscosity of the liquid being filtered and should be sized so that liquid entering the in-line vent filter 15 through port 7 will back up and fill chamber 10. At this condition, the liquid in chamber 10 will be at a pressure head greater than atmospheric pressure and below the bubble point pressure of the hydrophobic filter 3. Since a hydrophobic filter can not pass an aqueous solution at a pressure below the bubble point of the hydrophobic filter, fluid will not exit through ports 4. Likewise since the pressure head in chamber 10 is greater than atmospheric pressure air can not enter chamber 10 via ports 4. The restriction 11 should not restrict the flow of fluid through the liquid filtration device 129 (described below) which may be attached to the opposite end of the tubing 13. When fluid flow into port 7 of the vent filter 15 ceases the pressure head in chamber 10 shall decrease to zero enabling air to enter chamber 10 via ports 4 and hydrophobic filter 3 thus draining restriction 11 and tubing 13.

Figure 1B:
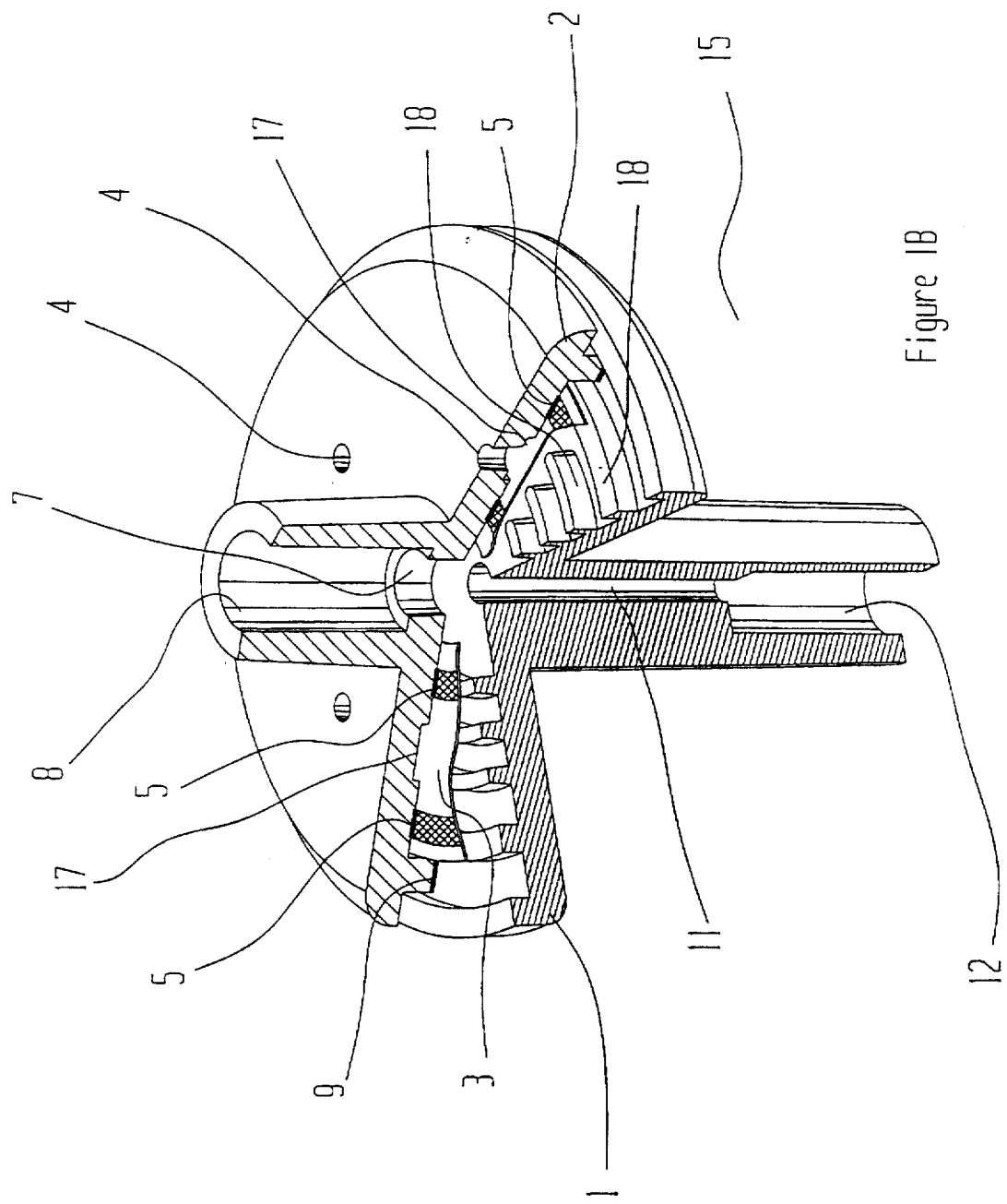
FIG. 1B depicts an isometric view of an in-line vent filter having portions removed therefrom and useable in accordance with the principles of the present invention.

FIG. 1B depicts an in-line vent filter which is similar in structure and operation to the vent filter depicted in FIG. 1A but also contains an inside channel 17 and a plurality of support ribs 18.

As depicted in FIG. 1B the inside portion of inlet section 1 of the vent filter 15 may contain channel 17 which provides a gap between the hydrophobic filter 3 and inlet section 1 which leads to vent ports 4. The outlet half 2 contains a plurality of support ribs 18 which assist in supporting the hydrophobic filter 3.

FIG. 2 is a schematic representation of the filtration device 129 which is suited for blood filtration and leukocyte and/or other blood component removal therefrom. Filtration device 129 includes inlet section or half 101 which is bonded to an outlet section or half 102 by a seal 120. This seal 120 is preferably an ultrasonic seal. However, other seals such as heat seals or adhesive seals or any other hermetic seal may be used. Inlet section 101 includes tubing socket 113 into which the outlet end of tubing 13 is affixed as well as port 122. The inlet end of tubing 13 is affixed to the outlet of the vent filter 15. Inlet section 101 contains side walls 131 extending about the periphery of bottom wall 130. Side walls 131 and bottom wall 130 define chamber 108. Any fluid exiting the vent filter 15 via tubing 13 will enter chamber 108 through port 122.

Outlet section 102 of the filtration device 129 may include a tube 110 affixed thereto which defines a passage 111. Tube 110 is preferably round and multi-diameter, however, other shapes may suffice. Outlet section 102 may also include a port 121, port 123, port 124, tubing socket 114 and tubing socket 115. Outlet section 102 includes a bottom wall 132 and side walls 133 extending about the periphery thereof. Side walls 133 and bottom wall 132 define chamber 109 of outlet half 102. A cover 112 may be affixed to outlet half 102 by seal 125. Seal 125 is preferably an ultrasonic seal. However, other seals may suffice. The cover 112 and multi diameter tube 110 define a chamber 111 which is in fluid flow relationship with chamber 109 via port 121. A hydrophobic filter 104 is sealed to an end of multi diameter tube 110, extending into chamber 108, by peripheral seal 105. Peripheral seal 105 is preferably a heat seal. Again, however, other types of reliable leak proof seals such as ultrasonic or adhesive seals may suffice. A hydrophilic filter 106 may be sealed to outlet section 102 by peripheral seal 107 to cover port 123. When dry, the hydrophilic filter 106 allows the passage of air therethrough except at peripheral seal 107, which should preferably be a heat seal. However, other types of reliable leak proof seals such as ultrasonic or adhesive seals may suffice. When wet, the hydrophilic filter 106 does not allow the passage of air therethrough unless the air pressure is above the bubble point pressure of the hydrophilic filter 106.

The hydrophobic filter 104 covers the end of tube 110 and, therefore, should be the same shape as the end of tube 110. Filtering elements 103, which may be leukocyte removing elements for blood filtration, should be shaped to divide the filtration device 129 into chamber 108 and chamber 109. The filtration elements 103 defines, along with inlet section 101, chamber 108 and, along with outlet section 102, chamber 109. Each filtration element 103 may have a hole therein which is positioned to enable the hole to align with tube 110 when the filtration elements 103 are placed into the filtration device 129. Therefore, it is preferred that the hole have the same shape and size of the small end of tube 110. The filtration elements 103 fit into and are contained by a filter element receptacle which is defined by side walls 145 of outlet section 102, and by shelf 147 of outlet section 102 and sealing rib 148 of inlet section 101.

The filtration device 129 in FIG. 2 contains four (4) filtration elements 103. When using the filtration device 129 for blood filtration, the filtration elements 103 may include leukocyte removing elements which are known in the art. Depending on the application, the filtration device 129 could be manufactured to accept more or less than four filtration elements 103. The outside periphery of the filtration elements 103 may be sealed to the filtration device 129 by a pinch seal 119 wherein the outside periphery of the filtration elements 103 is pressed between sealing rib 148 of inlet section 101 and shelf 147 of outlet section 102 creating a seal. Likewise the filtration elements 103 may be sealed to the tube 110 by a pinch seal 126. In this case, a washer 118 which may be press fitted about multi diameter tube 110 forces the filtration elements 103 between washer 118 and the lip 99 of tube 110 to form seal 126. Alternatively washer 118 could be ultrasonically welded, heat sealed or sealed with an adhesive to tube 110. Also, filtration elements 103 could be sealed to the filtration means 129 and multi diameter tube 110 by other reliable sealing techniques.

A first outlet from the chamber 109 is formed by port 124 which is in fluid flow relationship with Tee 127 via siphon tube 116. A second outlet from chamber 109 is formed by port 123 which is in fluid flow relationship with Tee 127 via tube 128. Tee 127 is in fluid flow relationship with a fluid or liquid receiving means via tubing 117. The tube 128, tee 127 and tube 116 function as a means for placing the first outlet formed by port 124 in fluid flow relationship with the second outlet formed by port 123. The receiving means could be a blood bag or even an open container. However, when using the system for blood filtration, a sterile receiving blood bag should be used.

Although FIG. 2 illustrates the inlet port 122 near the top of inlet half 101, port 122 may be placed in other locations. Moreover, port 122 need not be located on the vertical center line of inlet half 101. However, port 122 should not be placed adjacent to or directly below hydrophobic filter 104, particularly if the gap between wall 130 of inlet half 101 and hydrophobic filter 104 is small.

Figure 3:
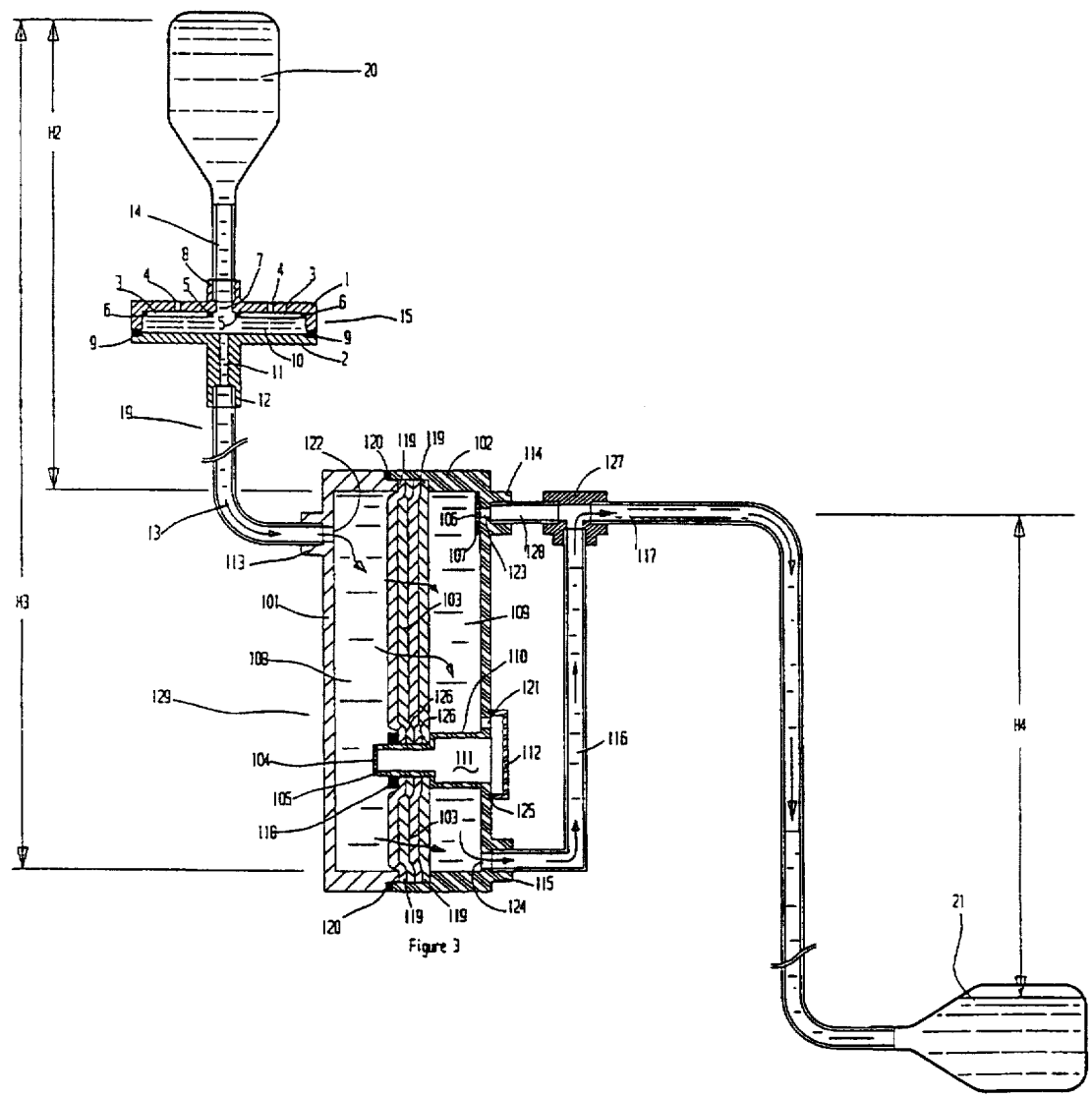
FIG. 3 depicts a schematic representation of the filtration device and in-line vent filter used for filtering blood where a blood supply bag is filled.

FIG. 3 illustrates one embodiment of the apparatus or system in accordance with the present invention including the vent filter 15, the filtration means 129, a feed blood bag 20, a receiving blood bag 21, and all the necessary interconnecting tubing. Typically, the user would purchase the system without feed blood bag 20. The user would receive the system sterilized with the inlet end of tubing 14 sealed to maintain system sterility. Therefore, with the exception of ports 4 the system is closed. Moreover, the hydrophobic filter 3 of vent filter should be a sterilizing grade filter which is sealed with a leak tight seal to the inlet section 1 of the vent filter 15. Therefore, the inside of the system should remain sterile.

When filtering blood the user would first close tubing 13 (near the outlet side of vent filter 15) with a tubing clamp (not illustrated) and then make a sterile connection between the inlet end of tubing 14 and the feed blood bag 20 using a sterile docking device known in the art. The actual sterile connection is made between tubing 14 and a short length of tubing which is a part of feed blood bag 20. The resulting system is illustrated in FIG. 3. Feed blood bag 20 may be suspended from an appropriate mechanism. The filtration means 129 may also be suspended from the mechanism or by tubing 13. A receiving blood bag 21 may be suspended by the mechanism or may rest on a surface such as a bench top or the like. Once the sterile connection is made between feed blood bag and tubing 14 and the system components are suspended, blood will flow from feed blood bag 20 and fill tubing 14, vent filter 15, and the upper part of tubing 13 to the point where a tubing clamp (not shown) clamps tubing 13. The air that was in tubing 14, vent filter 15 and the upper part of tubing 13 will vent through a sterilizing grade hydrophobic filter 3 and then through ports 4 to the atmosphere. Some of this air may also bubble to the top of feed blood bag 20.

Referring still to FIG. 3, once the tubing clamp (not shown) is opened blood will begin to flow from feed blood bag 20, through tubing 14, through vent filter 15, tubing 13 and finally through port 122 into chamber 108. In FIG. 3, the blood flow is indicated by the solid arrows. As blood begins to fill chamber 108 from the bottom up, air will vent from chamber 108 through the unwetted portions of filtration elements 103 (i.e. through the portion of the filtration elements 103 above the blood level) and through hydrophobic filter 104. The air that vents through hydrophobic filter 104 will pass through chamber 111 and then through port 121 and finally into chamber 109. The air that vents through the unwetted portions of filtration pads 103 will pass directly into chamber 109. All of the air that vents from chamber 108 to chamber 109 will then vent from chamber 109 through port 124 and then through siphon tube 116 into tee 127; and from chamber 109 through hydrophilic filter 106 and then through port 123 and then through tube 128 into Tee 127. The air will then vent from Tee 127 through tube 117 into receiving blood bag 21.

Once the blood level in chamber 108 is high enough to cover hydrophobic filter 104 air will stop venting from chamber 108 through hydrophobic filter 104 and all venting of chamber 108 will occur through the unwetted portions of filtration elements 103 (which in this blood filtration application may include leukocyte removing elements or elements used to remove other blood components). Chamber 108 will continue to fill with blood until all of the air in chamber 108 has been vented and chamber 108 is full of blood.

After the layers of the filtration elements 103 become wet, leukocyte depleted blood will start to pass from the elements 103 into chamber 109. This leukocyte depleted blood flow into chamber 109 will begin at or near the bottom of chamber 109. Because the surface area of the elements 103 is much greater than the surface area of the hydrophilic filter 106, and because the initial flow rate of blood through the elements 103 is high, and because the bubble point pressure of the hydrophilic filter 106 must be greater than pressure head at hydrophilic filter 106 relative to receiving blood bag 21, the following sequence of events will occur. Once the blood level in chamber 109 fills to the level where port 124 is covered the air pressure in chamber 109 will start to increase because the flow rate of leukocyte depleted blood entering chamber 109 will be greater than the flow rate of air exiting chamber 109 through hydrophilic filter 106 (because of the necessary maximum pore size of hydrophilic filter 106). This increase in air pressure in chamber 109 will cause blood to flow out of port 124 and into siphon tube 116. The blood level in tube 116 will then rise faster than the blood level in chamber 109. The leukocyte depleted blood in tube 116 will reach Tee 127 and fill Tee 127, the hydrophilic filter 106 will not be wet by the leukocyte depleted blood on the Tee side of hydrophilic filter 106 if tube 128 is of sufficient length or port 123 is sufficiently small. Assuming that one or both of these conditions is true the leukocyte depleted blood in Tee 127 will exit Tee 127 and then flow down tubing 117 into the receiving blood bag 21. At this point the pressure head at the bottom of chamber 108 relative to the top of the supply bag 20 will be greater than, the relative pressure head at the top of chamber 108. However, the pressure of the air in chamber 109 will be above atmospheric pressure and the pressure head in Tee 127 relative to the receiving blood bag 21 will be less than the pressure head at the top of chamber 109 and at the bottom of chamber 109. Hence the pressure in Tee 127 will be lower than the pressure in chamber 109. Therefore air will be sucked from chamber 109 through hydrophilic filter 106, then through port 123, then through tube 128 into Tee 127. At this point there will be a mixed stream of leukocyte depleted blood and air flowing down tubing 117 into receiving blood bag 21. As air is evacuated from chamber 109 the leukocyte depleted blood level in chamber 109 will rise. This process will continue until the level of leukocyte depleted blood in chamber 109 either covers hydrophilic filter 106 or until hydrophilic filter 106 becomes wetted by capillary action. Once the hydrophilic filter 106 is wet it will no longer allow air passage therethrough unless the air pressure exceeds the bubble point pressure of the hydrophilic filter 106. The pore size of hydrophilic filter 106 should be chosen so that once hydrophilic filter 106 is wet it will not allow air passage therethrough for the duration of the process. To assure that there will be a minimum amount of air trapped at the top of chamber 109 it is preferred that the volume of chamber 109 around hydrophilic filter 106 be kept to a minimum.

As feed blood bag 20 continues to drain, tubing 14, vent filter 15, tubing 13 and chamber 108 will be full of unfiltered blood. Chamber 109, siphon tube 116, tee 127 and tubing 117 will be full of leukocyte depleted blood and receiving blood bag 21 will be partially filled with leukocyte depleted blood with a small air pocket at the top of receiving blood bag 21 due the air that was initially purged from the system. The pressure head at the top of chamber 108 relative to the supply bag 20 will still be less than the pressure head at the bottom of chamber 108 relative to the supply bag 20. The pressure head at the bottom of chamber 109 relative to the supply bag will be equal to the pressure head at the bottom of chamber 108 less the pressure drop across the leukocyte removing pads 103 and the pressure head in Tee 127 relative to the receiving bag will be slightly greater than previously when the receiving bag began to fill due to the fact that receiving blood bag 21 has begun to fill. Throughout the process the external pressure on feed blood bag 20 and receiving blood bag 21 will be atmospheric.

From the beginning of the filtration process when blood begins to drain from feed blood bag 20, the pressure in chamber 108 will always be greater than the pressure in chamber 109. Therefore, air will never flow from chamber 109 into chamber 108. Likewise leukocyte depleted blood will never flow from chamber 109 into chamber 111 as long as port 121 is sufficiently small.

Figure 4:
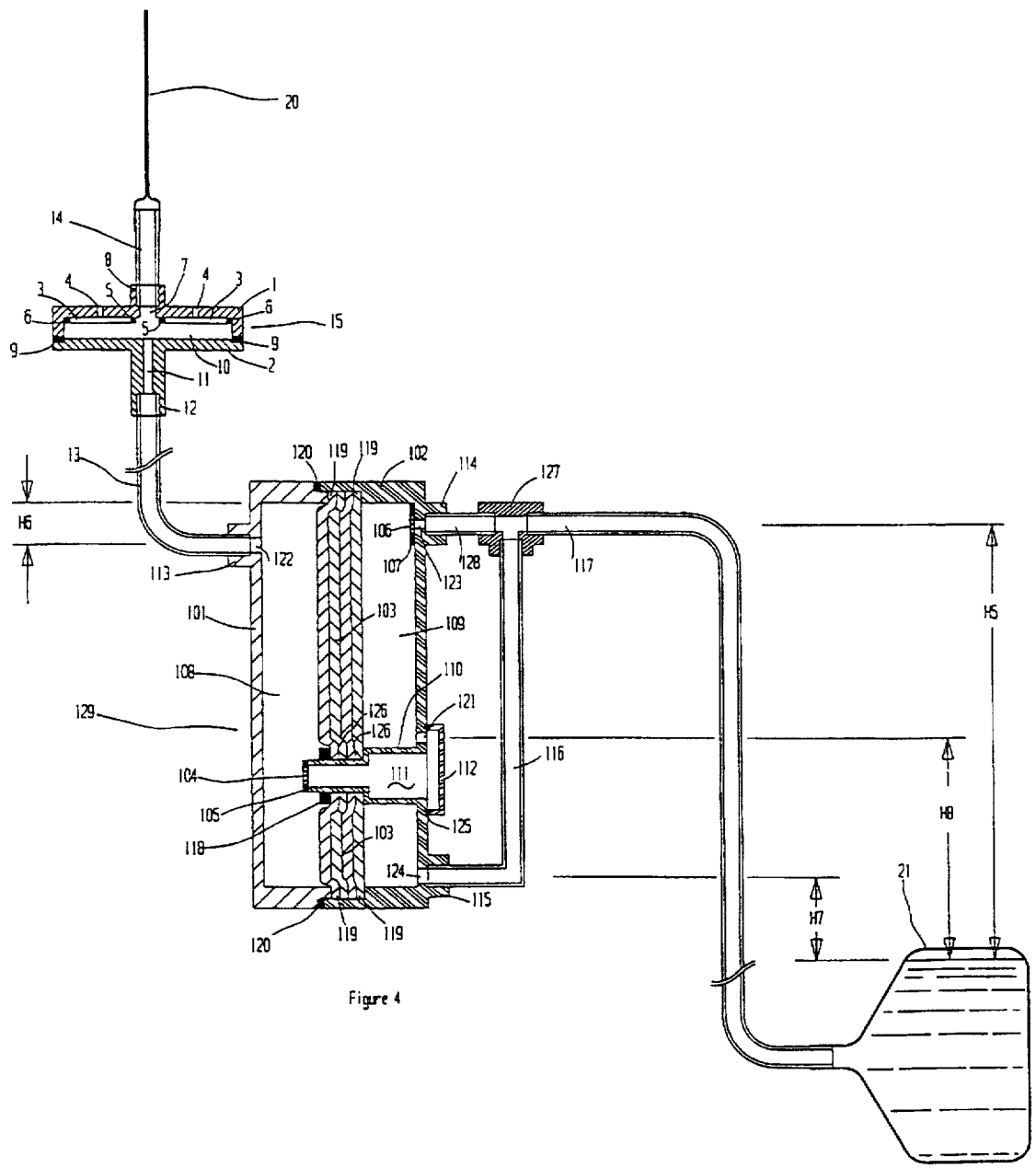
FIG. 4 depicts a schematic representation of the filtration device and in-line vent filter used for filtering blood where the blood supply bag is empty.

Referring to FIG. 4, when feed blood bag 20 has emptied tubing 14 will have an air tight cap (i.e. collapsed feed blood bag 20) at its top. The pressure head due to the blood in tubing 14 is now negated by the negative pressure head due to the leak tight cap at the top of tubing 14 and the pressure in chamber 10 of the vent filter 15 will be atmospheric. Air can now enter ports 4 of vent filter 15 and pass through sterilizing grade hydrophobic filter 3 into chamber 10 of vent filter 15. The air entering chamber 10 will displace the blood in chamber 10 causing chamber 10 to drain. Once chamber 10 has drained, restriction 11 will drain and then tubing 13 will drain. Since the input pressure to the system (at ports 4) is atmospheric and the pressure head relative to the receiving blood bag 21 in Tee 127 is less than atmosphere, draining will continue and receiving blood bag 21 will continue to fill. At this time, port 122 is at atmospheric pressure and the pressure head at the top of chamber 108 is less than atmospheric. Hence air will now enter chamber 108 through port 122 and bubble to the top of chamber 108 thus draining chamber 108 from the top down. Since the pressure head in Tee 127 remains relatively lower than that in chamber 108, chamber 108 will continue to drain.

Once the blood level in chamber 108 drains to below the level of hydrophobic filter 104 air will begin to flow from chamber 108 into chamber 111 and then through port 121 into chamber 109. Air will flow from chamber 108 to chamber 109 through the aforementioned path because the void part of chamber 108 is at atmospheric pressure and port 121 has a lower pressure relative to the receiving blood bag 21. To ensure that chamber 108 completely drains before air entering chamber 109 through port 121 drains chamber 109 the following criteria should be used:

a) Hydrophobic filter 104 should be of the minimum surface area necessary to allow drainage of chamber 109 in a reasonable time period. It should also be of the minimum surface area necessary so that a minimum amount of active surface area is removed from filtration elements 103 to allow for tube 110.
   b) Multi diameter tube 110 should be placed as close to the bottom of chamber 108 as other design considerations permit.
   c) For maximum safety hydrophobic filter 104 should be of sterilizing grade.

When air starts to enter chamber 109 from port 121 the pressure head at port 121 is greater than the pressure head at the top of chamber 109. Hence air entering chamber 109 from port 121 will bubble up to the top of chamber 109 and displace leukocyte depleted blood in chamber 109 from the top down. Because hydrophilic filter 106 is now wet air can not flow from chamber 109 through hydrophilic filter 106, port 123 and tubing 128 into Tee 127. Hence tubing 117 is not allowed to drain via hydrophilic filter 106. If tubing 117 were allowed to drain via hydrophilic filter 106 the filtered blood in chamber 109 would only drain to the bottom level of Tee 127. Chamber 109 will continue to drain in this manner until the leukocyte depleted blood level reaches the top of port 124. Then the tube 116 will be drained and tubing 117 will drain to the leukocyte depleted blood level at the top of receiving blood bag 21. Tubing 117 should then be sealed close to the receiving blood bag 21 and receiving blood bag 21 along with the short length of sealed tubing 117 may be cut from the rest of the system and is ready for use. The rest of the system (i.e. feed blood bag 20, vent filter 15, fluid filtration means 129, Tee 127 and all remaining tubing should be discarded in a proper manner.

The air that initially fills the voids in the system is purged into receiving blood bag 21 when the system is primed with blood. To minimize the amount of air that is purged into receiving blood bag 21 the void volume should be kept to a minimum. To minimize the void volume the gap between wall 130 of inlet section 101 and hydrophobic filter 104 should be kept to a minimum. Therefore, port 122 of inlet section 101 should not be placed adjacent to or directly below hydrophobic filter 104.

FIGS. 5–9 illustrates an alternative embodiment of the filtration device 229 constructed in accordance with the principals of the present invention. This embodiment may be easily manufactured using disposable injection molded plastic components. Moreover, the filtration device 229 may be designed so that the user can easily hang all the system components from a hanging means such as a pole with hooks to allow for gravity feed of the fluids, such as blood, to be filtered. This embodiment operates in the same manner as the embodiment previously discussed.

Figure 5:
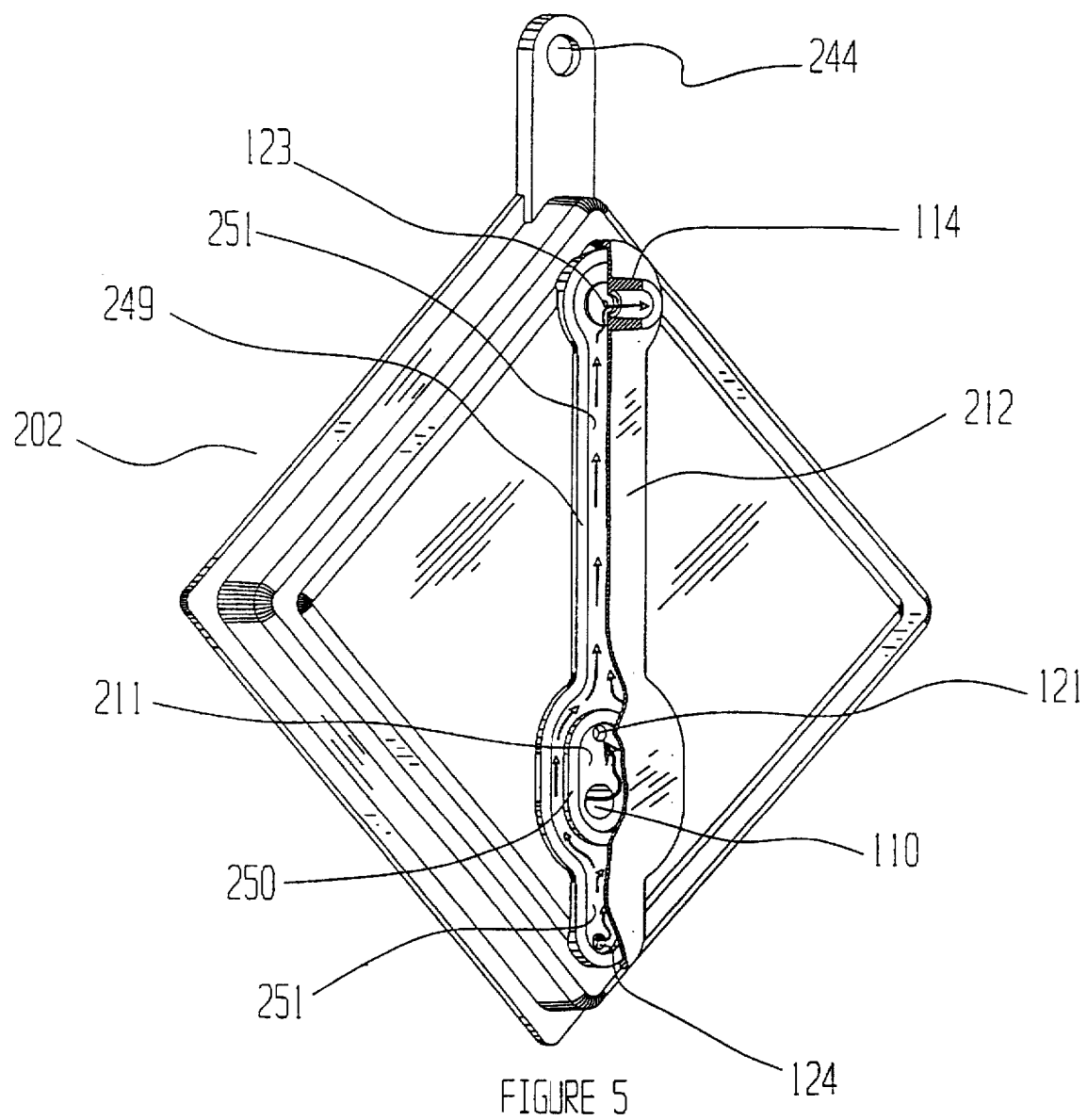
FIG. 5 depicts an outlet section of an embodiment of the filtration device constructed in accordance with the principles of the present invention whereby a means for placing a first outlet in fluid flow relationship with the second outlet of a second chamber of the device-is integrally formed with the outlet section of the device.
Figure 6:
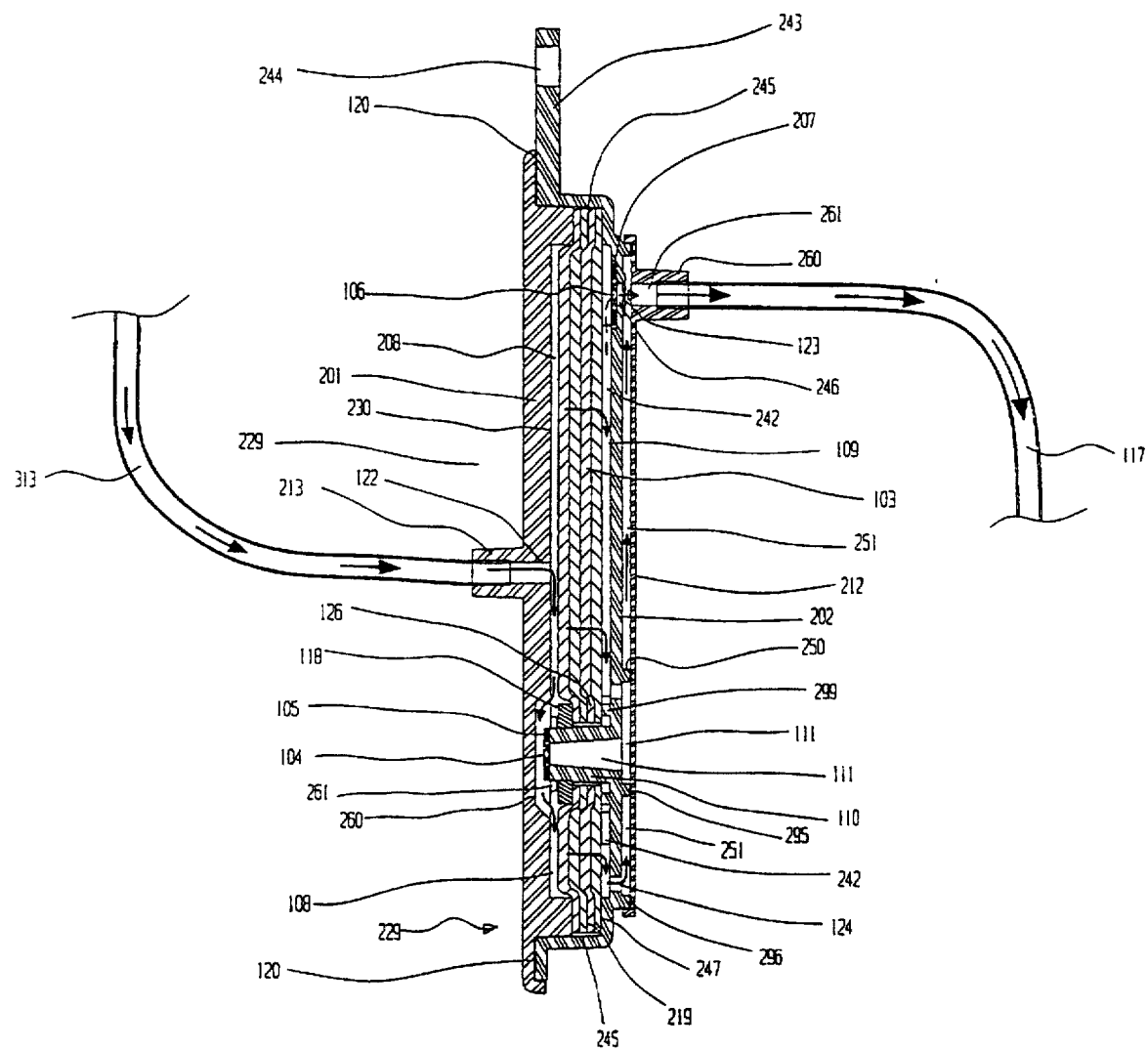
FIG. 6 depicts a sectional representation of the alternative embodiment of the filtration device having the outlet section depicted in FIG. 5.

Referring to FIG. 5, in this embodiment the means for placing the first outlet, formed by port 124 of chamber 109, in fluid flow relationship with the second outlet, formed by port 123 of chamber 109, is integrally formed to outlet section 202. A conduit 251 is formed by a ridge 249 extending from the outlet section 202 and an outlet cover 212 which is sealed to the ridge 249. Ridge 249 and outlet cover 212 are sealed to prevent fluid flowing within conduit 251 from leaking therefrom. An interior ridge 250 extends from the outlet section 202 but within conduit 251. Raised ridge 250 also contacts outlet cover 212 to form a chamber 111 which is isolated from conduit 251 so that fluid within conduit 251 cannot enter chamber 111. Within chamber 111 is located an end of the interior of tube 110 which passes through filtering elements 103 (FIG. 6). Referring to FIG. 6, port 121 places chamber 111 in fluid flow relationship with chamber 109. Accordingly, chamber 109 is placed in fluid flow relationship with chamber 108 by the interior of tube 110, chamber 111, and port 121, which are all in fluid flow relationship with each other. Within conduit 251 is the first outlet of chamber 109 formed by port 124 and the second outlet of chamber 109 formed by port 123. Both port 123 and port 124, constitute passages which lead into chamber 109 placing conduit 251 in fluid flow relationship with the chamber 109. A hanging means 244 may be oriented to allow the housing formed by the first section 201 and second section 202 to be gravity hung. In the hanging position, the second outlet formed by port 123 is located above first outlet formed by port 124 for improved operation of the filtration device.

Referring still to FIG. 6, the inlet section 201 is engaged with outlet section 202 to form a housing. The edges of the filtration elements 103 are located between the inlet section 201 and outlet section 202. Seal 120 is used to seal the inlet section 201 to the outlet section 202. Inlet port 122 leads to chamber 108 which is in fluid flow relationship with tube 110. Hydrophobic filter 104 is located at one end of tube 110 to prevent liquid to be filtered, such as blood, from passing therethrough. A seal 105 seals the hydrophobic filter to the tube 110. The washer 118 is placed around tube 110 so that filtration elements 103 are located between the washer 118 and a lip 299. Hydrophilic filter 106 is preferably located over port 123 to prevent air from within the chamber 109 from flowing through the port 123 when hydrophilic filter 106 is wet. The hydrophilic filter may be recessed within a well 207. Preferably, a heat seal is used to seal the hydrophilic filter to the outlet section 202. Port 123 is in fluid flow relationship with conduit 251. A nipple 260 may be formed around port 123 for allowing filtered fluid, such as blood, from flowing therethrough into a collection tube 117 and eventually into a collection bag 221.

Operation of the embodiment depicted in FIGS. 5–9 occurs similar to the embodiment of the device depicted in FIGS. 1–4. However, in lieu of external tube 116, conduit 251 transports filtered blood from the outlet 124 to the fluid collecting tube 117. Also, chamber 108 and chamber 109 are reduced in volume to minimize the volume of air purged into receiving blood bag 221. Using such a configuration, first section 101 may require a recessed area 260 to allow tube 110 to protrude into chamber 108.

Figure 7:
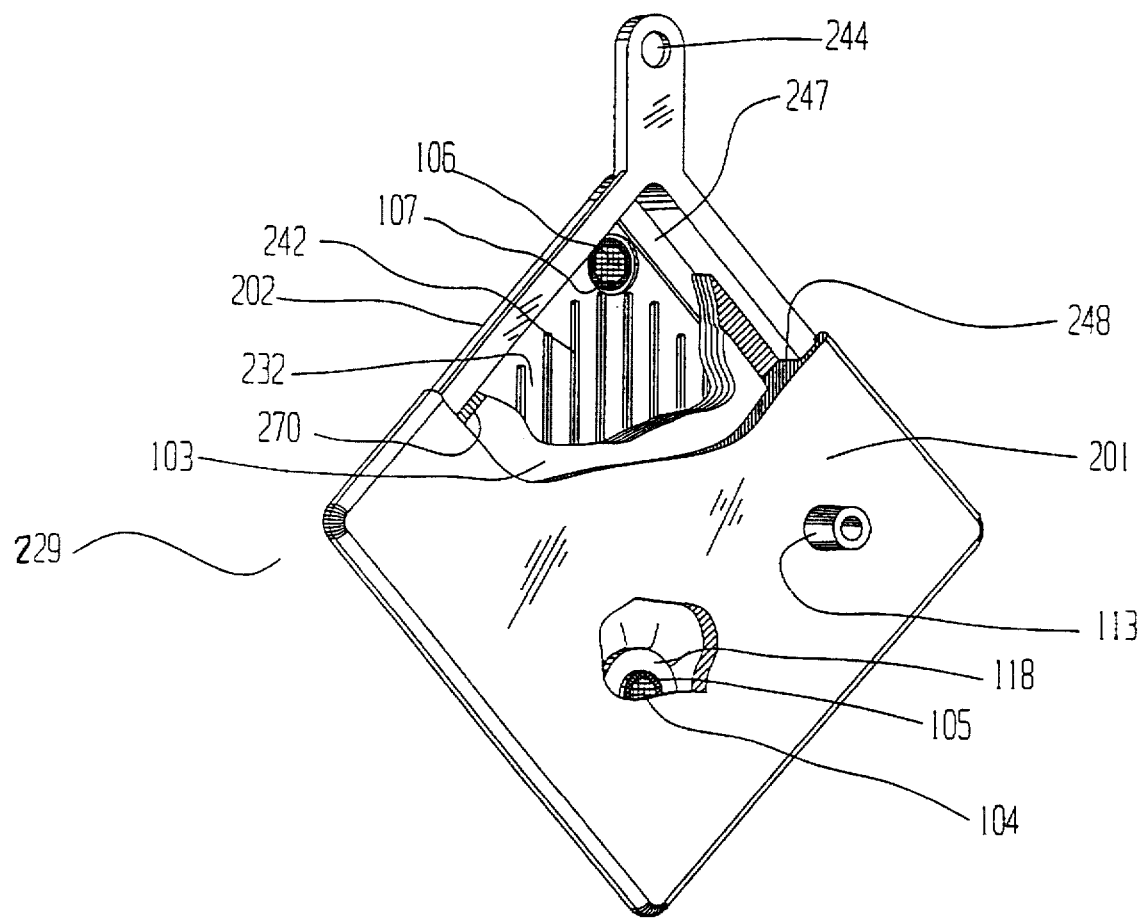
FIG. 7 depicts an isometric view, having portions thereof removed, of the embodiment of the filtration device depicted in FIG. 6.
Figure 8:
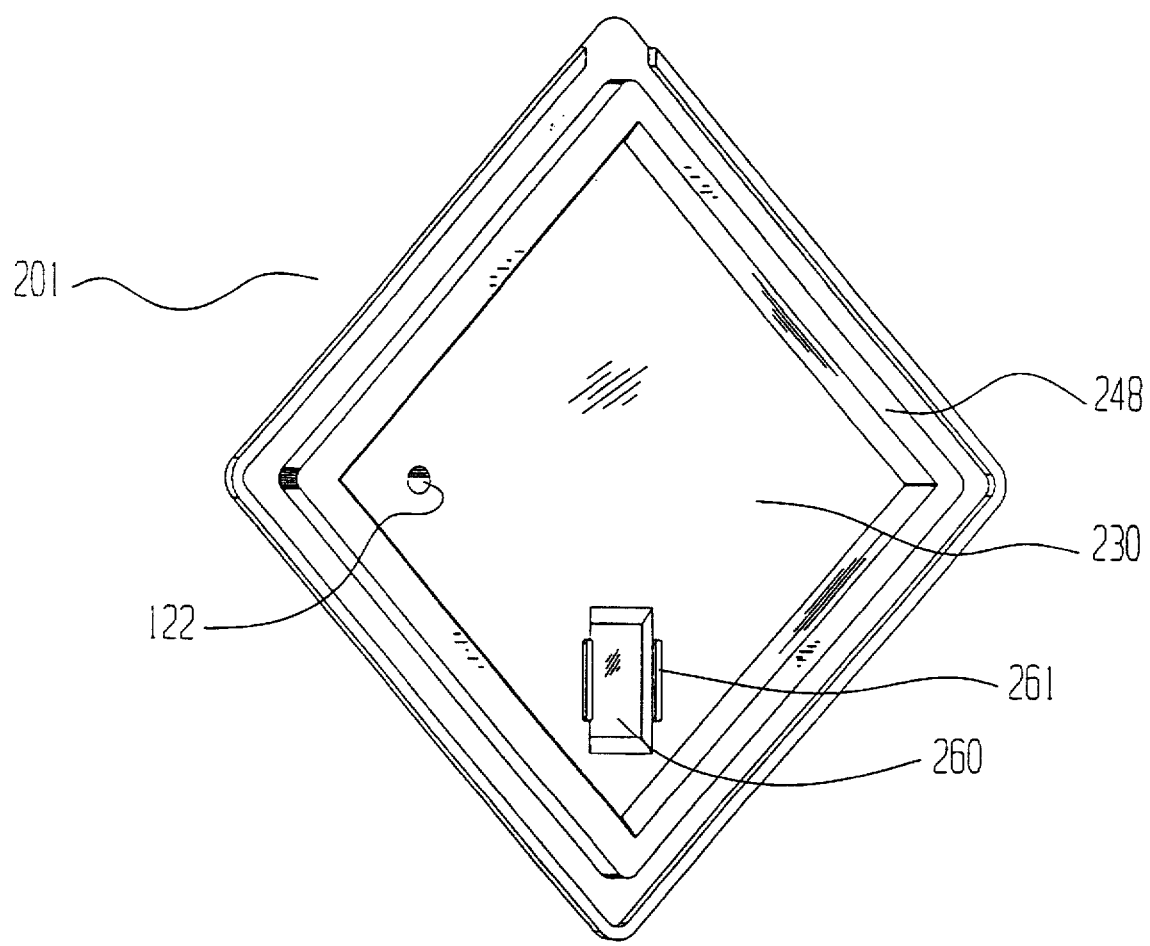
FIG. 8 depicts an isometric view of the inside surface of the first section of the embodiment of the filtration device depicted in FIG. 7.

FIG. 7 depicts a sectional view of the aforementioned embodiment of the filtration device 229. On the inside surface of second section 202 a plurality of ribs 242 are located. The ribs 242 serve to stabilize the position of filtration elements 103 while allowing liquid such as blood to be filtered to flow through chamber 109. The ribs prevent the pressure exerted within chamber 108 from deforming the filtration elements 103. FIG. 8 depicts the inside surface of first section 201. Recess 260 contains a ridge 261 located on one or more edges thereof and extending from the inside surface 230 of the first section. As shown in FIG. 6, ridge 261 contacts washer 118 to maintain a force against the portion of filtration elements 103 between the washer 118 and lip 299.

Figure 9:
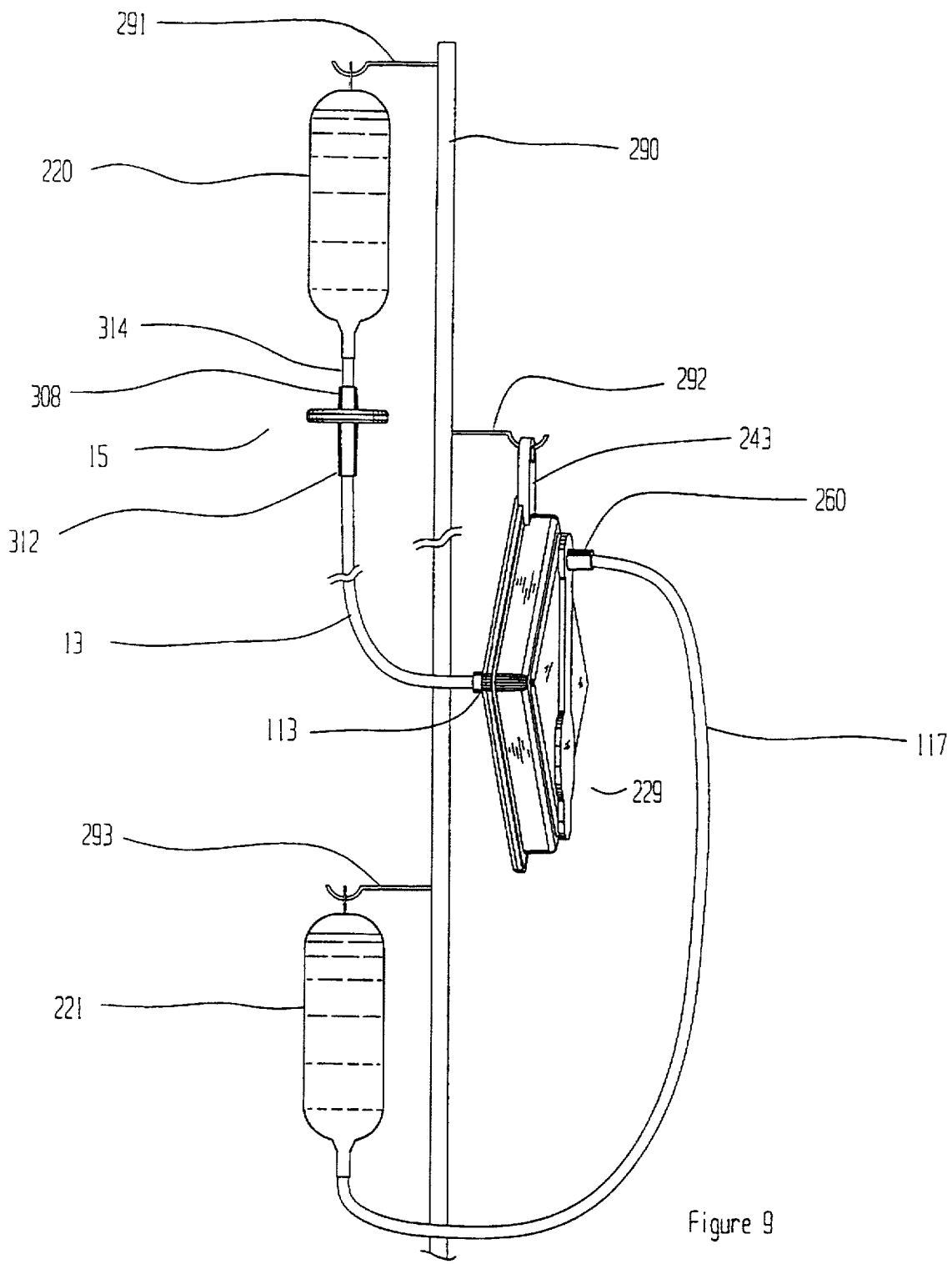
FIG. 9 depicts the embodiment of the filtration device depicted in FIG. 7 having the in-line vent filter, tubing, blood supply means and blood collecting means in an operational assembly.

Referring to FIG. 9, the fluid filtration device when used to filter blood may be used by placing a blood supply bag 220 in fluid flow relationship with an in-line vent filter 15. Blood flowing through the vent filter is carried by a conduit 13 to filtration device 229 via inlet nipple 113. A collection tube 117 is connected to an outlet nipple 260, at one end, and at the other end to a blood collecting bag 221. The filtration of blood occurs without the need for manually opening and closing vents or for moving the blood collecting bag to different heights relative to the blood supply bag or housing 229.

Figure 10:
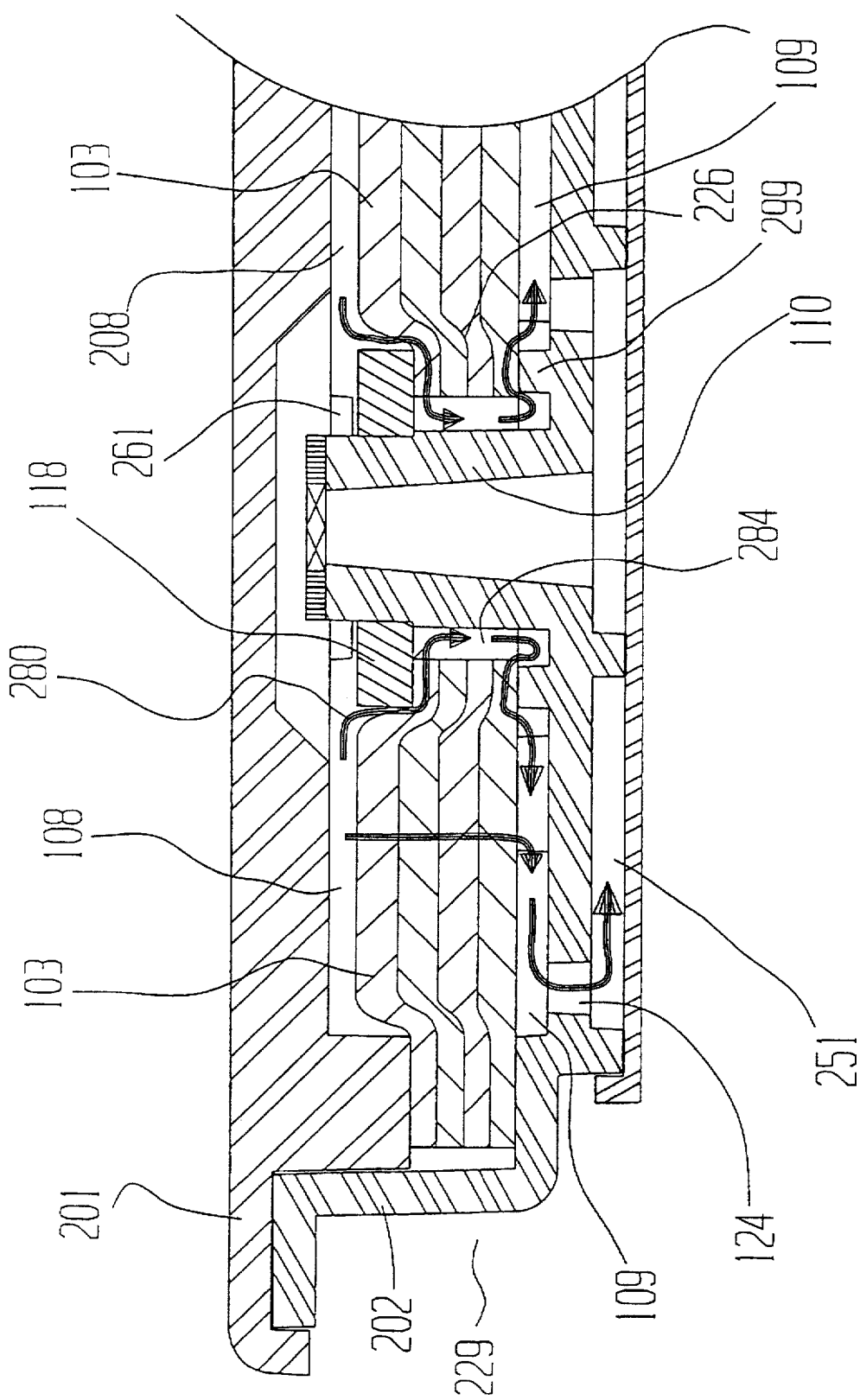
FIG. 10 depicts a cross-sectional view of a lower section of the embodiment of the filtration device depicting one technique for sealing a plurality of filtration elements therein.

FIG. 10 is an exploded view of the lower part of the filtration device 229 depicted in FIG. 6 for the purposes of depicting sealing techniques useable in connection with the present invention. The fluid filtration device 229 contains four filtration elements 103. However, more or less than four filtration elements 103 may be used depending on the application. Each filtration element 103 may provide a logarithmic reduction of leukocytes from the blood that passes through that layer. For example, if unfiltered blood initially contains 1,000 leukocytes/ml, it will contain 100 leukocytes/ml after passing through one filtration element 103. Hence four leukocyte filtration elements 103 should give four orders of logarithmic reduction of leukocytes and/or other blood components. FIG. 10 illustrates the blood flow path through four filtration elements 103. Blood may bypass filtration through each of the elements. For example, blood flow may start in chamber 108 and follows the shortest path from chamber 108 through the first filtration element into gap 284 between tube 110 and the edge of the filtration elements 103 and through the last filtration elements 103 into chamber 109.

If the distance travelled by blood, which flows through the filtration elements 103 and gap 284 is less than the thickness of all of the filtration elements 103, then blood may bypass some of the elements and may not be adequately filtered. One solution to the problem is to increase the diameter of washer 218 and to increase the width of ring 250. This will increase the length that blood bypassing the intermediate layers of filtration elements must travel. However, since tube 110 and ring 299 should be located near the bottom of the device, there is a limit to their diameters. Moreover, increasing the diameter of washer 118 increases the possibility for wrinkles to form in elements 103 causing blood to flow therethrough and avoid complete filtration.

Figure 11:
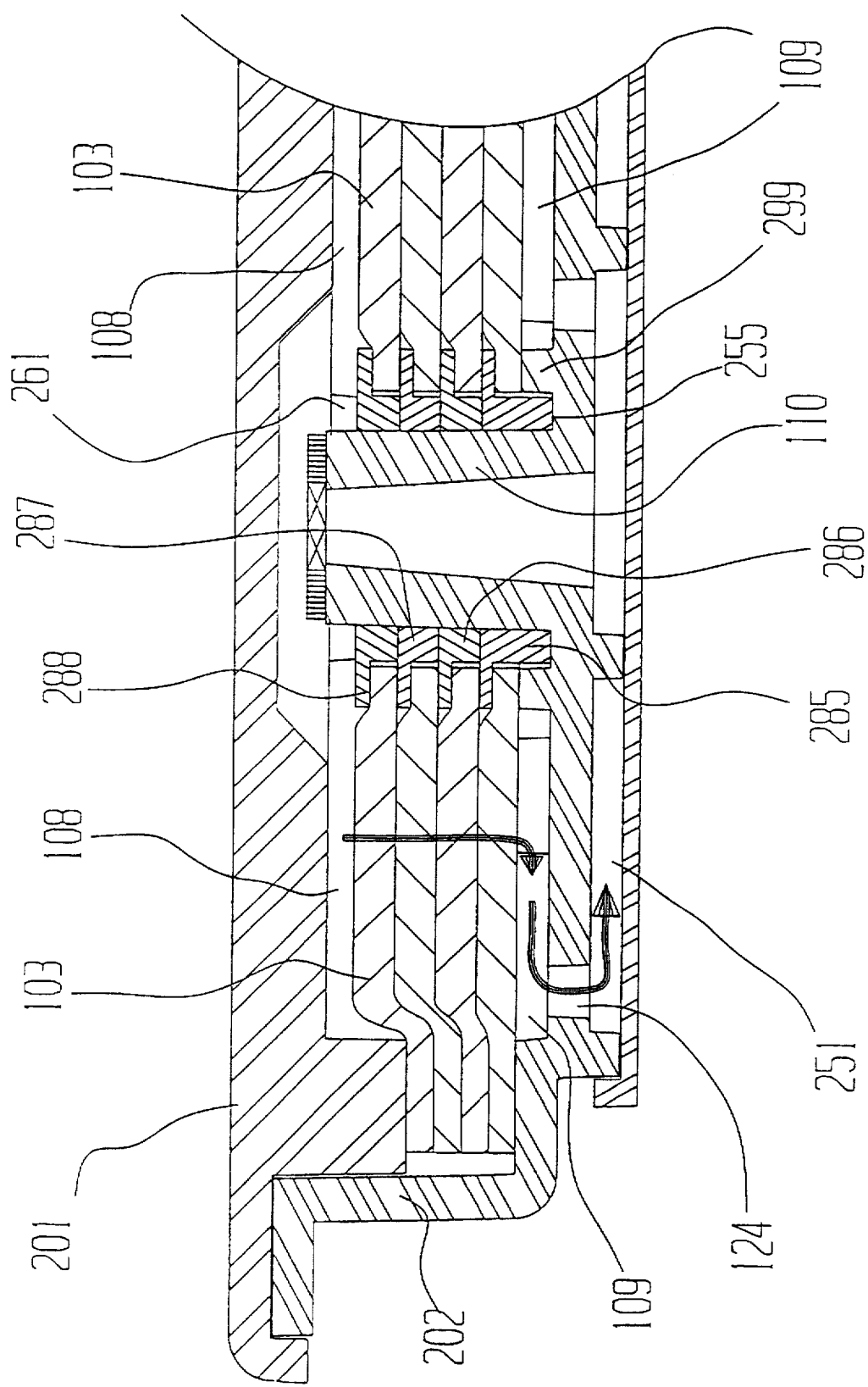
FIG. 11 depicts a cross-sectional view of the lower portion of an embodiment of the filtration device depicting an alternative technique for sealing a plurality of filtration elements.

A preferred solution to the above mentioned bypass problem is illustrated in FIG. 11. In FIG. 11, flanged washers 285, 286, 287 and 288 independently seal each layer of the leukocyte removing elements 103 around tube 110. Each flanged washer should be sized to contact either the washer stacked thereupon, surface 255, or ridge 261 depending upon its position. Also, preferably flanged washers 285, 286, 287, and 288, are press fit around tube 110. However, other reliable sealing techniques could be used to seal the flanged washers to tube 254. Also, instead of sealing each of the flanged washers to tube 110, each interior flanged washer could be sealed to the adjoining washers. Moreover, the flanged washer contacting ridge 261 may be sealed thereto and/or the flange washer contacting surface 255 may be sealed to surface 255. Also, it may be possible to use a number of flanged washers which are less than the number of filtration elements. If a press fit is used between the flanged washers and tube 254, then the flanged washers and tube 254 may be made of dissimilar materials which are preferably radiation sterilizable. The flange of the flanged washers should be made as thin as practical so as to minimize wrinkling of the filtration elements 103. Ridge 261 of inlet half 201 prevents the flanged washers from rising on tube 254 once inlet half 201 is sealed to outlet half 202.

Figure 12:
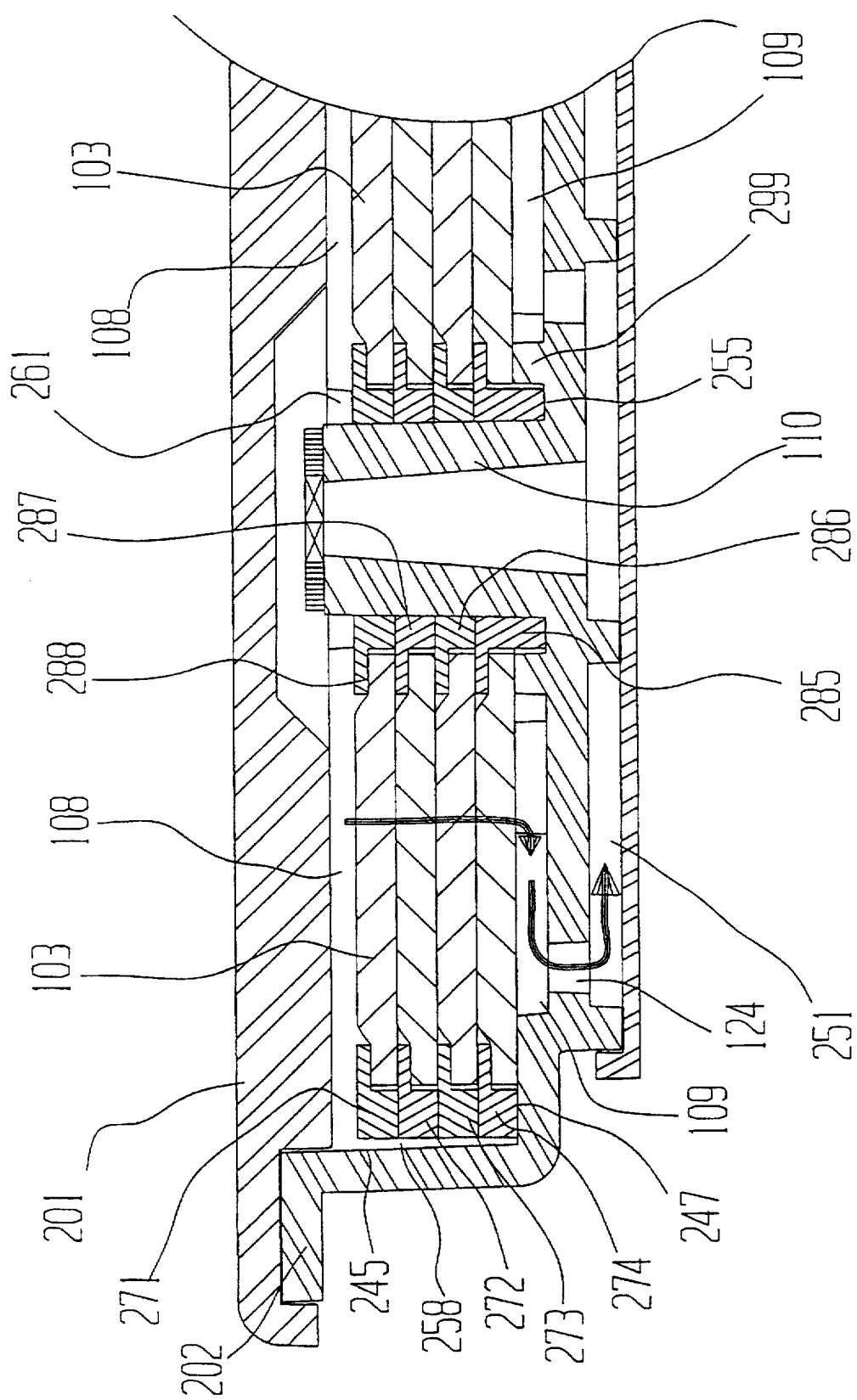
FIG. 12 depicts a cross-sectional view of the lower portion of a filtration device constructed in accordance with the principles of the present invention depicting one technique for sealing the outer edges of a plurality of filtration elements.

FIG. 12 depicts the lower portion of the embodiment of the filtration device 229 depicted in FIG. 11 using an alternative means for sealing the edges of filtration elements 103. Flanged rings 271, 272, 273, 274 are placed over the edges of each filtration element 103. Each flanged ring may be sealed to the second section 202, or each flanged ring may be sealed to its adjacent flanged ring and the lower flanged ring 274 sealed to second section 202. Also, each or some of the flanged rings 271, 272, 273, 274 may be press fit against side wall 245 of second section 202. Each flanged ring should extend throughout the outer edge of the filtration elements. Also, it may be possible to use a number of flanged rings which is less than the number of filtration elements.

Figure 13:
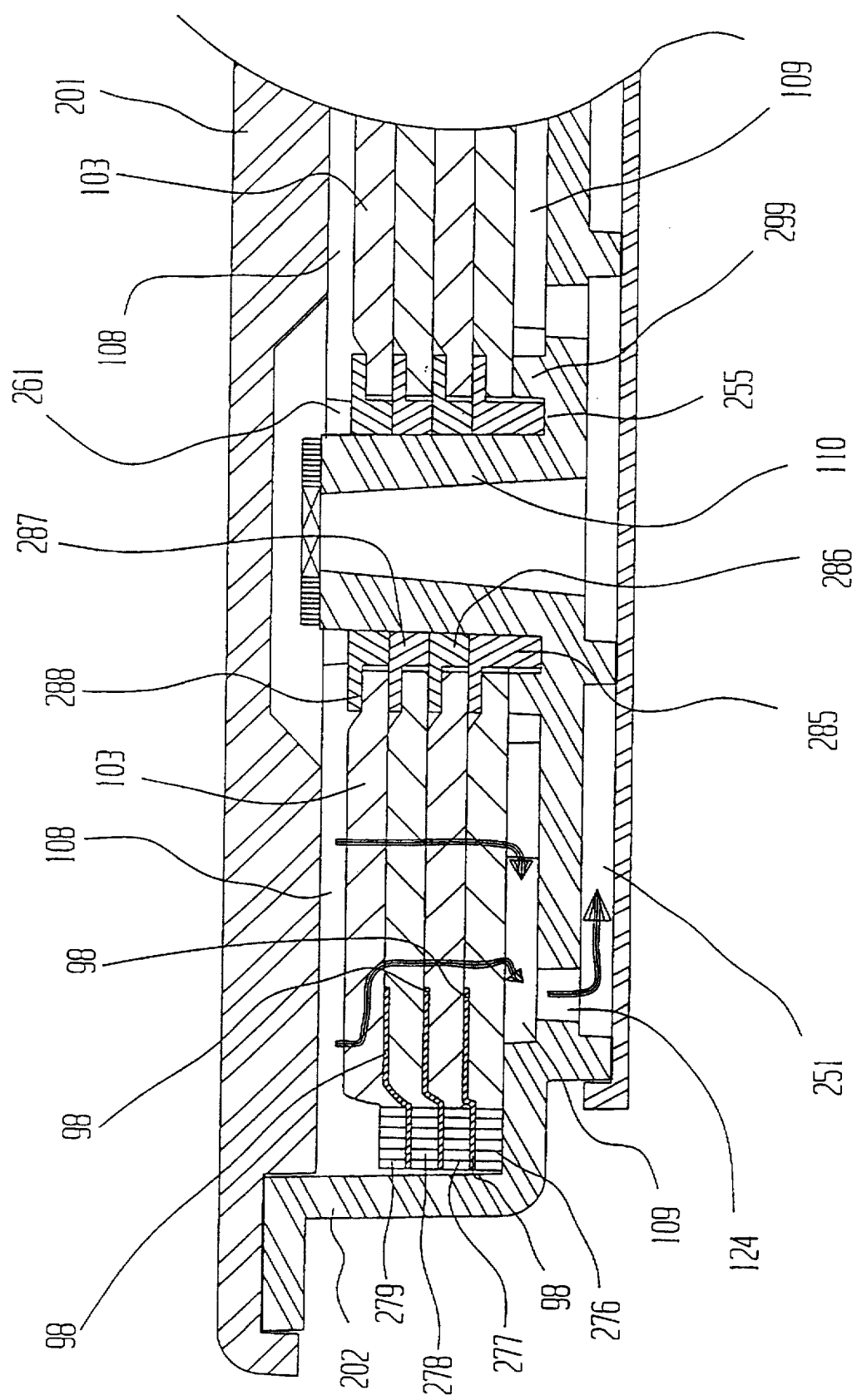
FIG. 13 depicts a cross-sectional view of the lower portion of a filtration device constructed in accordance with the principles of the present invention depicting an alternative technique for sealing the outer edges of a plurality of filtration elements.

FIG. 13 depicts an alternative technique for sealing the edges of filtration elements 103. Using this technique, the edge 276 of the bottom filtration element is bonded to second section 202, preferably by a heat seal which extends around the entire periphery of the filtration element 103. The heat seal, however, will compress the fibers at the edges 276, 277, 278, 279, of the filtration element which will effectively reduce the filtration capability of the elements at the interface between the compressed and noncompressed region. To prevent reduced filtration capability, layers of polyethylene film 98 may be placed between each layer of the filtration elements 103 prior to sealing the edges of each layer 276, 277, 278, 279 to one another. The polyethylene film layers 98 prevent blood from filtering through the interface regions affected by the heat sealing. Other thermoplastic films may be used in lieu of a polyethylene film 98. However, the film layers should extend around the entire periphery of filtration elements 103. Also, the edge 276 of the lower filtration element may be sealed to second section 202 and the other edges 277, 278, 279 of the filtration elements may be sealed to one another. However, other patterns and techniques for sealing the edges 276, 277, 278, 279 to one another or to the second section 202 may be used.

Figure 14:
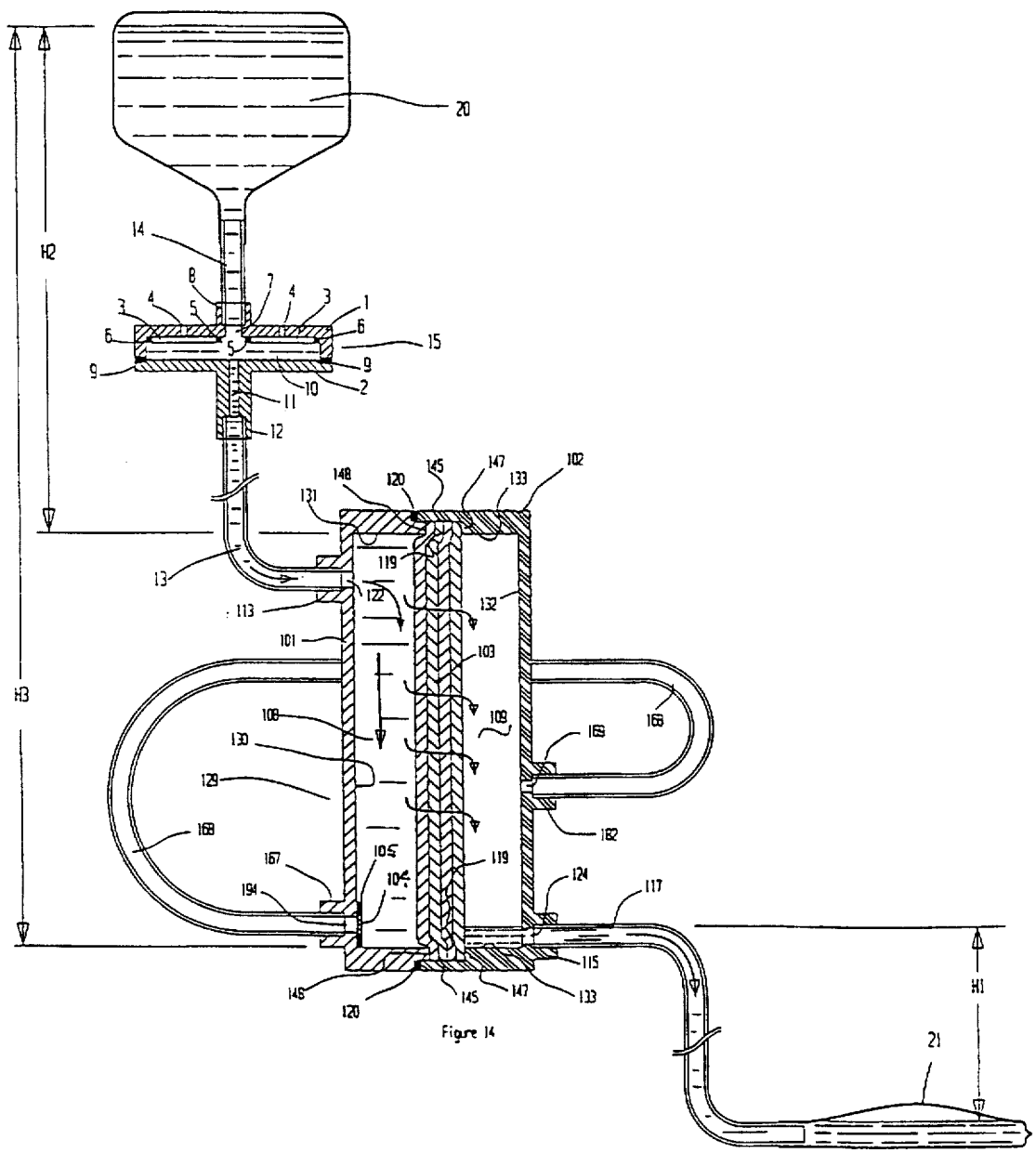
FIG. 14 depicts a schematic representation of yet another embodiment of the filtration device constructed in accordance with the principles of the present invention along with a vent filter blood supply means and blood collecting means.

FIG. 14 illustrates yet another embodiment of the invention. This filtration device does not contain a second outlet from the second chamber 109 or a means for placing the first outlet 124 in fluid flow relationship to a second outlet. Tubing 168 looping around the back of filtration device 129 acts a means for placing the first chamber 108 in fluid flow relationship with the second chamber. Assuming the filtration of blood within the device 129, as discussed supra, a sterile connection would be made between tubing 14 and feed blood bag 20. The system components would then be suspended as depicted in FIG. 14. Blood would flow from tubing 13 through port 122 into chamber 108 of inlet half 101. Chamber 108 will fill from the bottom up until chamber 108 is full. As with previous embodiments tubing socket 113 and port 122 can be located anywhere on inlet half 101. Filter 104 is a hydrophobic filter which prevents blood from flowing therethrough. As chamber 108 begins to fill, filtration elements 103 will begin to wet from the bottom up. As chamber 108 fills, the air in chamber 108 will vent through the non wet portions of filtration elements 103 into chamber 109. This air will exit from chamber 109 into receiving blood bag 21 through port 124 and tubing 117. As filtration elements 103 wet, the air that was in these filtration elements will also vent into chamber 109 and then into receiving blood bag 21 through port 124 and tubing 117. Blood will begin to flow through filtration elements 103 from the bottom up. At this point both blood and air will be passing from filtration elements 103 into chamber 109 of outlet section 102 and a mixed stream of blood and air will pass through port 124 and tubing 117 into receiving blood bag 21. This process will continue until filtration elements 103 are completely wet with blood. The blood level in chamber 109 will then rise to a level just above the level of tubing 117 as depicted in FIG. 14. At this point tubing 117 will be full of blood (i.e., no air) and air will cease to flow into receiving blood bag 21.

When feed blood bag 20 is empty air will pass from ports 4 through hydrophobic filter 3 of the vent 15. Vent filter 15, tubing 13 and chamber 108 of inlet section 101 will drain through filtration elements 103 into chamber 109 of outlet section 102. Chamber 108 will drain from the top down. Once the blood level in chamber 108 falls below the non sealed portion of hydrophobic filter 106 air will begin to pass from chamber 108 through port 194, tubing 168 and port 169 into chamber 109. This air flow from chamber 108 to chamber 109 will bring chamber 109 to atmospheric pressure thus draining chamber 109 and tubing 117 into receiving blood bag 21. To ensure that chamber 108 drains completely hydrophobic filter 106 should be placed at the bottom of chamber 108 and hydrophobic filter 106 should be of small enough pore size to give the necessary delay (i.e., to allow chamber 108 to finish draining before enough air passes through hydrophobic filter 106 into chamber 109 and causes chamber 109 to drain). If hydrophobic filter 106, tubing socket 167 and port 194 are located at a higher location on inlet half 101 filtration device 129 will still filter in the same manner, but chamber 108 will not completely drain at the end of the filtration process.

Although the invention has been depicted in connection with the embodiments disclosed herein, it will be apparent to one of ordinary skill in the art that the invention may be performed using various modifications and substitutions to the embodiments depicted herein. Any such modifications or substitutions are intended to be within the scope of the invention as defined by the following claims.

What is claimed is:

1. An in-line vent filter for use upstream of a blood product filtration device to drain blood product initially contained within an upstream supply bag from within said device comprising:

a body having a chamber therein and an inlet and outlet therein;

at least one vent opening within said body leading to said chamber; and at least one hydrophobic filter oriented to prevent blood product flowing from said supply bag within said body from passing through said at least one vent opening;

said body being configured without a filtration media therein to allow said blood product flowing into said inlet from said supply bag to flow unfiltered directly through said chamber and through said outlet;

flow restriction means, formed by a cross sectional area of said outlet being less than a cross sectional area of said inlet, for creating a pressure head sufficient to prevent air from entering said body and said chamber through said at least one vent opening until the blood product flow stops thereby causing air to automatically enter said at least one vent opening to drain said blood product from said filtration device.

2. The in-line vent filter of claim 1 wherein said at least one hydrophobic filter is sealed to said body.

3. The in-line vent filter of claim 2 wherein said at least one hydrophobic filter comprises an opening coaxially oriented with said inlet.

4. The in-line vent filter of claim 1 or 2 wherein said body comprises an inlet half and an outlet half.

5. The in-line vent filter of claim 4 further comprising a channel located on the inlet half of the body and facing within said body, said channel being in fluid flow relationship to said at least one vent opening.

6. The in-line vent filter of claim 5 further comprising a plurality of support ribs extend from the outlet half within the body.

7. The in-line vent filter of claim 4 wherein the outlet half is bonded to the inlet half.

8. The in-line vent filter according to claim 1, wherein the pressure head is greater than atmospheric pressure.

9. The in-line vent filter according to claim 8, wherein the pressure head is less than the bubble point of the hydrophobic filter.

10. An in-line vent filter comprising:

a body having an inlet and outlet therein, said body configured without a filtration media therein to allow blood product to flow unfiltered from said inlet to said outlet;

at least one vent opening within said body;

at least one hydrophobic filter located within said body and located over one of said at least one vent opening, said at least one hydrophobic filter being sealed to said body to prevent the blood product within said body from leaking between the body and the hydrophobic filter; and flow restriction means within said body for preventing air from entering said body through said at least one event opening during flow of the blood product through said body until the blood product flow stops thereby causing air to automatically enter said at least one vent opening to drain blood product downstream.

11. An apparatus for filtering biological liquid comprising:

a vent device located downstream of a biological liquid supply bag and upstream of a biological liquid filtration device;

a chamber within said vent device;

an inlet and outlet to said chamber to allow for liquid flow therethrough;

at least one vent opening within said vent device being in direct fluid flow relationship with said chamber and said outlet and inlet therein;

at least one hydrophobic filter oriented to prevent biological liquid within said chamber from passing through said at least one vent opening;

said body being configured without a filtration means to allow said biological liquid to flow from said supply bag unfiltered directly through said body and through said outlet; and flow restriction means for creating a pressure head of said biological liquid sufficient to prevent air from entering said chamber within said body through said at least one vent opening while said biological liquid flows from said liquid supply bag through said body thereby preventing air from entering said biological liquid until the flow of biological liquid stops and then allowing air to automatically enter said chamber through said at least one vent opening to drain remaining biological liquid.

* * * * *